US00PP19886P3

(12) United States Plant Patent
Feng

(10) Patent No.: US PP19,886 P3
(45) Date of Patent: Apr. 7, 2009

(54) ***DORITAENOPSIS* PLANT NAMED 'SOGO LINLUO'**

(50) Latin Name: ***Doritis*×*Phalaenopsis***
Varietal Denomination: Sogo Linluo

(76) Inventor: Chiang-Kuei Feng, No. 1-1, Chenggong Xieneun, Jiyang Village, Meinong Town, Kaohsiung County (TW)

( * ) Notice: Subject to any disclaimer, the term of this patent is extended or adjusted under 35 U.S.C. 154(b) by 213 days.

(21) Appl. No.: 11/482,827

(22) Filed: Jul. 10, 2006

(65) Prior Publication Data

US 2008/0010712 P1 Jan. 10, 2008

(51) Int. Cl.
*A01H 5/00* (2006.01)

(52) U.S. Cl. ..... Plt./311

(58) Field of Classification Search ..... Plt./311
See application file for complete search history.

*Primary Examiner*—Kent L Bell
(74) *Attorney, Agent, or Firm*—Muncy, Geissler, Olds & Lowe, PLLC

(57) ABSTRACT

A new and distinct cultivar of *Doritaenopsis* plant named 'Sogo Linluo,' with flowers of light yellow overlaid with pink toward base and a purple red labellum, freely flowering habit, upright, freely branching and sturdy flowering stems, and excellent postproduction longevity.

3 Drawing Sheets

FIELD OF THE INVENTION

The present invention relates to botanical classification/cultivar designation: *Doritaenopsis* Orchid cultivar Sogo Linluo.

BACKGROUND OF THE INVENTION

The present invention comprises a new and distinct cultivar of *Doritaenopsis* Orchid, a bigeneric hybrid of *Doritis*× *Phalaenopsis,* both of the family Orchidaceae, and hereinafter referred to by the cultivar name, 'Sogo Linluo'. The genus *Doritaenopsis* is also a member of the family Orchidaceae.

*Doritaenopsis* comprise a group of bigeneric hybrids generally intermediate in character between the parent genera, which are suitable for cultivation in the home or greenhouse. The parent genera of *Doritaenopsis* are predominantly epiphytic or rock dwelling, and are native to tropical Asia, Malay Archipelago, and Oceania. The species typically have 2-ranked fleshy oblong or elliptic leaves affixed to a short central stem (monopodial growth), which vary in size from 5 to 8 inches to over 2 feet. The leaves may be entirely green or mottled with silver grey.

*Doritaenopsis* orchids, often referred to as "Moth Orchids" in the horticultural trade, are frequently used to furnish cut flowers for the florist trade, or sold as flowering potted plants for home or interior plant scapes.

*Doritaenopsis* produce upright racemes, often with many showy flowers, which open in succession beginning with the lowermost. The flowers possess three sepals, and three petals, the lateral ones being alike. The lowermost petal, called the labellum, is three lobed and is often more brightly colored than the other flower segments. Flower colors are frequently various shades of pink, white and yellow.

*Doritaenopsis* orchids are typically propagated from seeds. However, *Doritaenopsis* is capable of being asexually reproduced from offshoots, which frequently arise from the lower bracts of the inflorescence. The resulting plants are detached from the mother plant and may be planted in a suitable substrate.

'Sogo Linluo' is a product of a planned breeding program conducted by the inventor in Kaohsiung County, Taiwan. The objective of the breeding program is to create new uniform pot-type *Doritaenopsis* Orchid cultivars having attractive flower coloration. The inventor had been addressed himself to the Orchids breeding since 1985.

'Sogo Linluo' was discovered by the inventor from within the progeny of a cross-pollination of one *Phalaenopsis* Orchid and one *Doritaenopsis* Orchid on Feb. 1999, in a controlled environment in Kaohsiung County, Taiwan.

Asexual propagation by tissue culture in a laboratory in Pingdong County, Taiwan has been used to increase the number of plants for evaluation and has demonstrated in a controlled environment in Kaohsiung County, Taiwan that the unique combination of characteristics as herein disclosed for the new *Doritaenopsis* Orchid are firmly fixed and are retained through successive generations of asexual reproduction.

SUMMARY OF THE INVENTION

The following traits have been repeatedly observed and are determined to be basic characteristics of 'Sogo Linluo' which, in combination, distinguish this *Doritaenopsis* Orchid as a new and distinct cultivar:

1. Light yellow flowers overlaid with pink toward the base and the purple red colored labellum.
2. Freely flowering habit.
3. Upright, freely branching and sturdy flowering stems.
4. Excellent postproduction longevity.

Plants of 'Sogo Linluo' differ primarily from plants of the parent cultivars in flower color. Currently, there is no commercial cultivar known to the inventor to which 'Sogo Linluo' can be meaningfully compared.

BRIEF DESCRIPTION OF THE DRAWINGS

The accompanied photographic illustrations show typical plant and flower characteristics of 'Sogo Linluo' with colors being as true as possible with illustrations of this type.

DETAILED DESCRIPTION OF THE PREFERRED EMBODIMENTS

Figure 1:
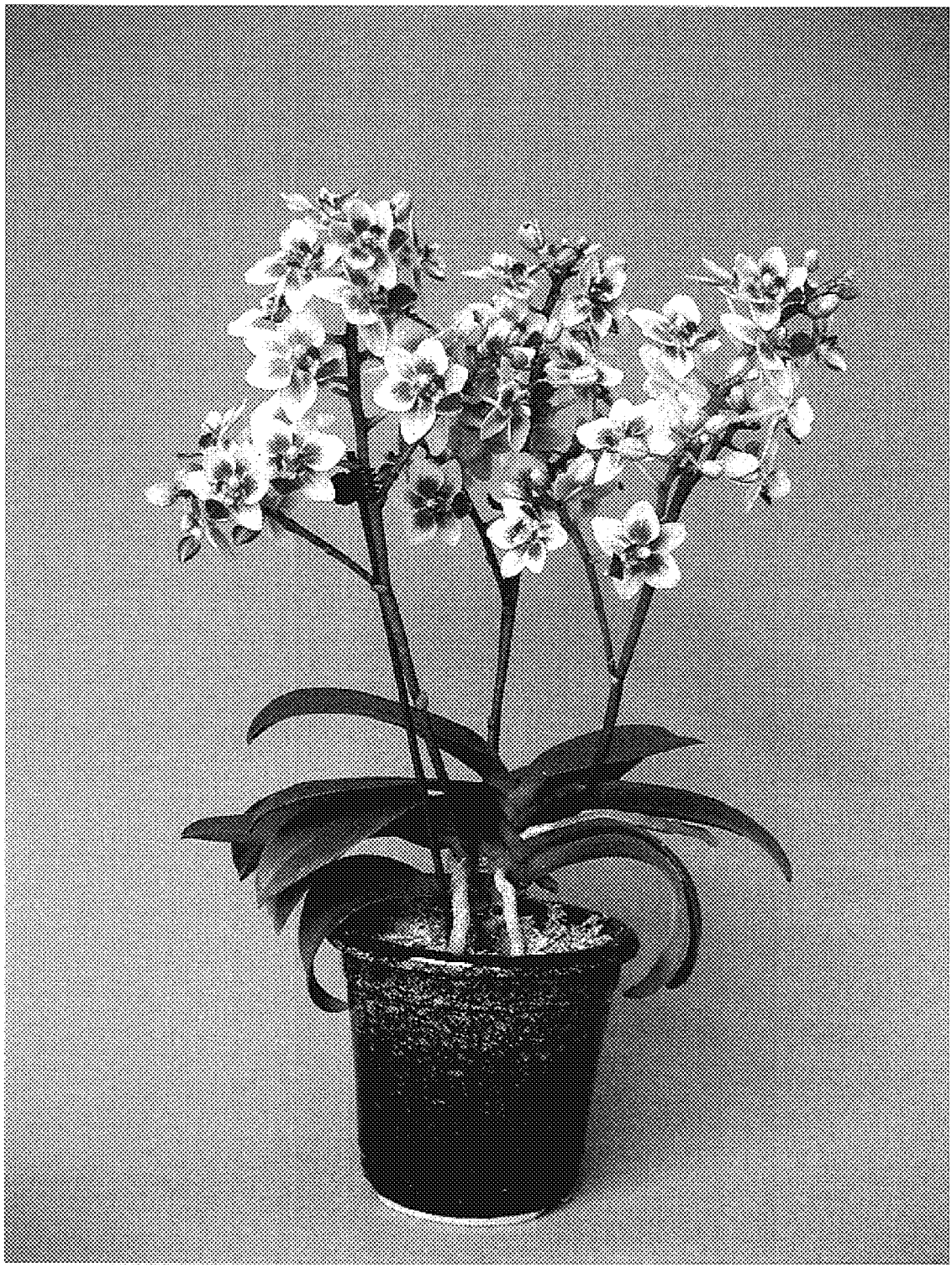
FIG. 1 is a side view of a plant of 'Sogo Linluo' flowering in a 13 cm pot.
Figure 2:
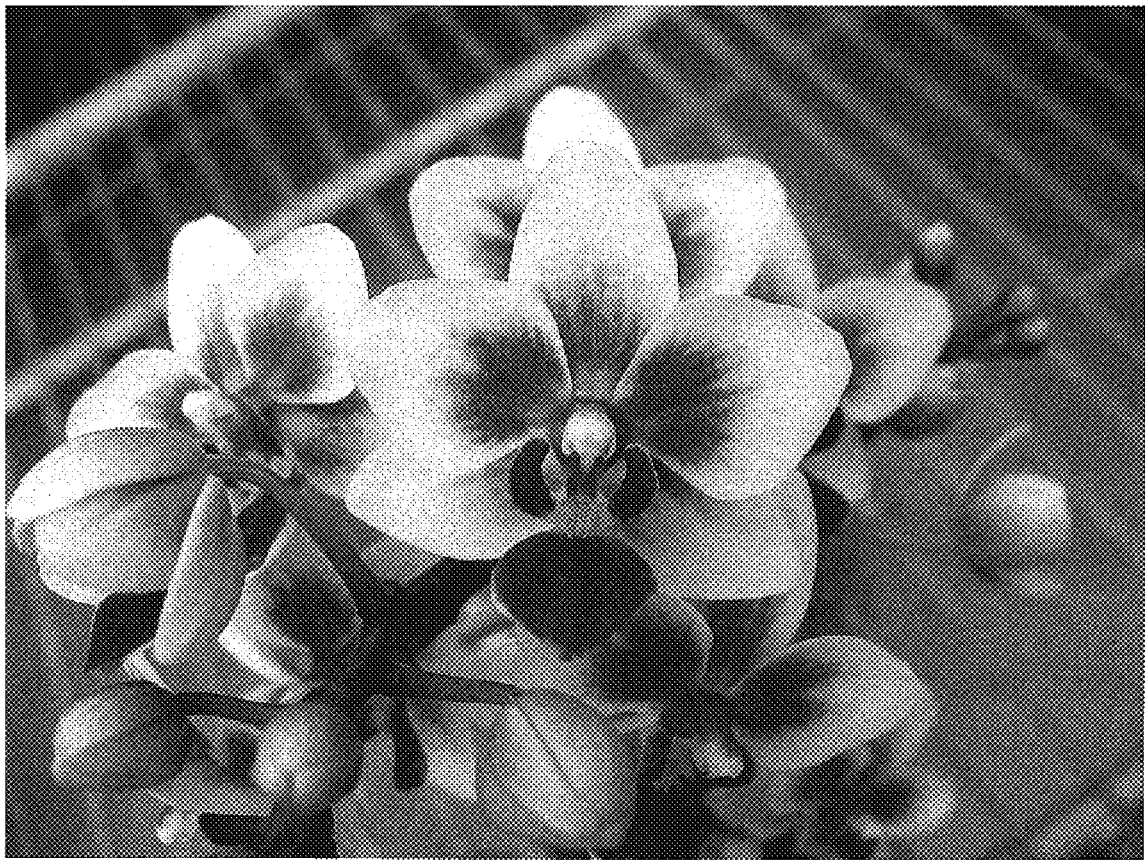
FIG. 2 is a close-up view showing the characteristics of the flowers.
Figure 3:
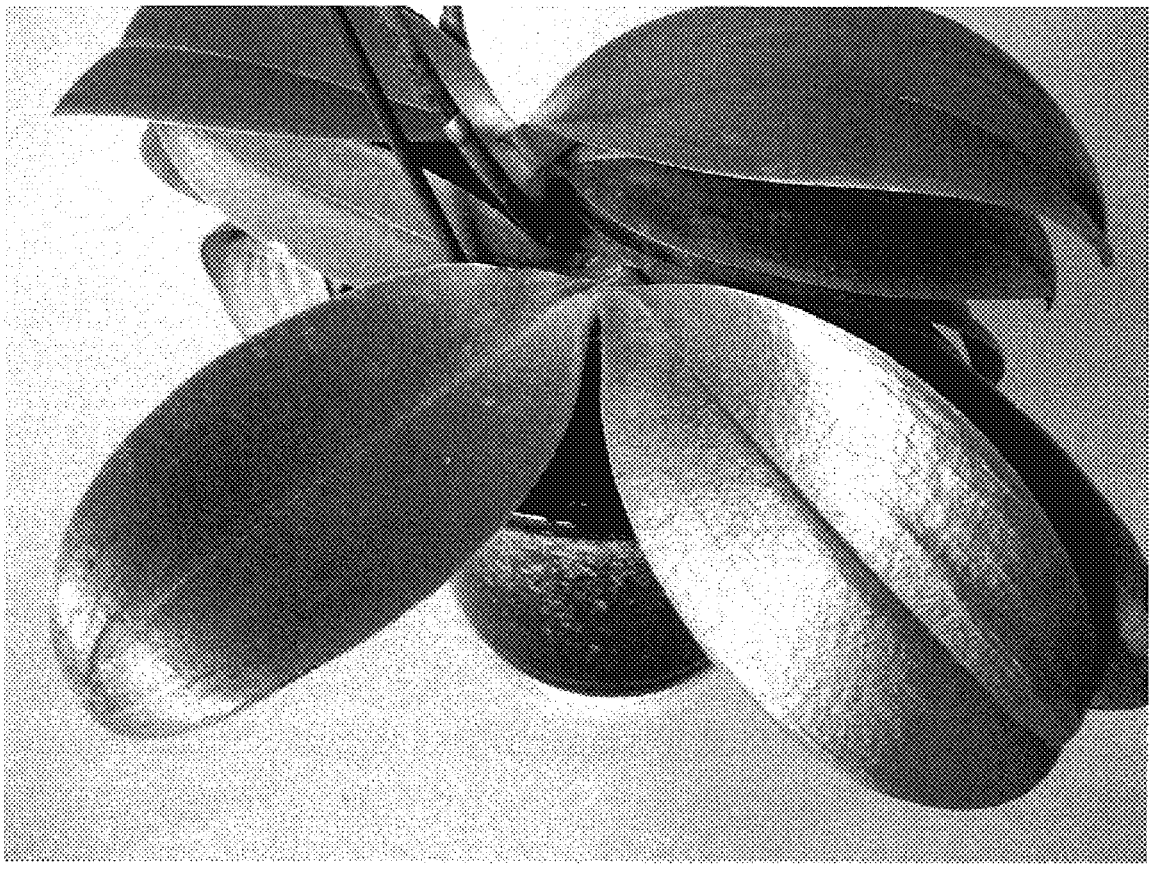
FIG. 3 is a close-up view showing the characteristics of the leaves.

'Sogo Linluo' has not been observed under all possible environmental conditions. The phenotype may vary significantly with variations in environment such as temperature, light intensity, fertilization and day length without any change in the genotype.

The observations and measurements describe plants grown in Kaohsiung County, Taiwan under the conditions, which approximate those generally used in commercial practice.

In the following description, color references are made to The Royal Horticultural Society (R.H.S.) Color Chart.

Plants used for the aforementioned photographs and following detailed botanical description were 18 months in maturity and grown in 13 cm pots, in a controlled greenhouse with day-night temperature around 25–18 degree Celsius, and light intensity between 15,000–20,000 lux natural light, in Kaohsiung County, Taiwan.

Origin: Seedling from a cross of selected *Doritaenopsis* and *Phalaenopsis* but unnamed parentage.
Classification: *Doritaenopsis* hybrid cv. 'Sogo Linluo'.
Propagation: Asexual propagation by tissue culture.
Plant description:
- *Plant height.*—Soil level to top of foliar plane is about 20 to 25 cm.
- *Plant height.*—Soil level to top of inflorescences is about 40 to 45 cm.
- *Plant diameter.*—Is about 20 to 25 cm.
- *Growth habit.*—Compact, small, dark-green leaves and a relatively short raceme.
- *Flowers per stem.*—Approximately 30 to 40.

Foliage description:
- *Leaves.*—Lanceolate.
- *Quantity.*—Approximately 6 to 8 leaves are produced before flowering.
- *Length.*—10–15 cm.
- *Width.*—5–6 cm.
- *Shape.*—Short and elliptic.
- *Base.*—Cuneate.
- *Tip.*—Obtuse.
- *Texture.*—Leathery and thick.
- *Venation.*—The middle vein protrudes, while the other veins are not visible in the thick leaf blade.
- *Attitude.*—Horizontal and on two sides parallel.
- *Color* (*upper surface*).—Dark-green, RHS 137A.
- *Color* (*lower surface*).—Light-green, RHS 146B.

Inflorescence description:
- *Flower type.*—Single zygomorphic flowers, roughly pentagonal in shape.
- *Flower arrangement.*—Compound racemes.
- *Flowering stems.*—Upright, freely branching and sturdy.
- *Flowering habit.*—Plants freely flowering; plants typically produce one to three branched flowering stems with at least 20 to 25 flowers each.
- *Fragrance.*—No fragrance.
- *Natural flowering season.*—From February to April in the southern part of Taiwan. The flower spikes can be induced under the controlled environment, of which day-night temperature at 25–18° C. for 2 weeks.
- *Post-production longevity.*—Plants of 'Sogo Linluo' maintain good leaf and flower substance for about three to six months on the plant under interior environmental conditions. Lastingness of cut flowers has not been observed.
- *Inflorescence length.*—About 15 to 20 cm.
- *Inflorescence diameter.*—About 13 to 18 cm.
- *Inflorescence depth.*—Typically 6.5 cm.
- *Flower bud.*—Flower bud shape. — Ovate. Flower bud length. — About 1.3–1.5 cm. Flower bud width. — About 1.0–1.1 cm. Flower bud color. — The main color is RHS-1B, with a color pattern-shaded of RHS-51B.

General impressions of Petals and Sepals: Horizontal elliptical in shape, having an inflorescence width of about 4.5 cm in front view.

Sepals:
- *Quantity.*—Three per flower, including one dorsal and two lateral.
- *Sepal length.*—About 2 cm.
- *Sepal width.*—About 1.5 cm.
- *Shape.*—Oval.
- *Margin.*—Straight.
- *Texture, upper and lower surfaces.*—Fleshy and glabrous.
- *Dorsal sepal main color.*—RHS 4D.
- *Dorsal sepal pattern color.*—72B.
- *Lateral sepal main color.*—RHS 4D.
- *Lateral sepal pattern color.*—70C.
- *Sepal outside surface main color.*—RHS 8A.
- *Sepal outside surface pattern color.*—RHS 61B.

Petals:
- *Number of petals.*—Two per flower.
- *Petal size.*—Lateral petals similar in size and shape.
- *Length.*—About 1.8 cm.
- *Diameter.*—About 1.5 cm.
- *Shape.*—Elliptical.
- *Margin.*—Weakly undulate.
- *Texture, upper and lower surfaces.*—Fleshy and glabrous.
- *Petal main color.*—RHS 4D.
- *Petal pattern color.*—72B.

Labellum (Lip):
- *Length.*—Approximately 1.1 to 1.3 cm.
- *Width.*—Approximately 1.0 to 1.2 cm.
- *Lip whiskers.*—Absent.
- *Lateral lobe.*—Present.
- *Lateral lobe main color* (*front surface*).—RHS-61A
- *Lateral lobe main color (back surface).*—RHS-158-B
- *Apical lobe shape.*—Ovate.
- *Base color of the apical lobe.*—RHS N79B.
- *Tip color of the apical lobe.*—RHS N79C.

*Callosities.*—Present.
*Length of callosities.*—About 0.3–0.4 cm.
*Width of callosities.*—About 0.25–0.3 cm.
*Depth of callosities.*—About 0.25–0.3 cm.
*Main color of callosities.*—3A.
*Spot color of callosities.*—42B.

Peduncles:
*Length.*—About 25–30 cm.
*Diameter.*—About 4.5 mm.
*Strength.*—Upright, strong, and sturdy.
*Texture.*—Smooth and glabrous.
*Color.*—RHS 146A.

Pedicels:
*Length.*—About 2.5 cm.
*Diameter.*—About 2 mm.
*Aspect.*—About 80° from vertical.
*Strength.*—Strong.
*Texture.*—Smooth and glabrous.
*Color.*—RHS 146C towards the base, overlaid with RHS 146A.

Reproductive organs:

The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

Column:
*Length.*—Approximately 0.7–0.8 cm long.
*Width.*—0.45–0.5 cm wide.
*Main color.*—RHS 61A.

Pollinia:
*Number.*—Two, about 0.6 to 0.7 mm oval masses of pollen present.
*Color.*—RHS 22A.

Ovary:
*Length.*—0.4–0.45 cm.
*Diameter.*—2.5 mm in diameter.
*Color.*—RHS 75B.

Roots:
*Texture.*—Fleshy.
*Width.*—Approximately 5 to 7 mm.
*Color.*—Green, between RHS 148B and RHS 148C.

Plant disease resistance/susceptibility: No specific resistance or susceptibility observed.

Temperature tolerance: Plants of the new *Doritaenopsis* Orchid cultivar Sogo Linluo have been observed to grow at temperatures from about 18–28° C., and flower from about 23–25° C., in a relative humidity of 60–80%. If the ambient temperature is below 10° C., it is necessary to be aware of chilling injury.

General observations: *Doritaenopsis* 'Sogo Linluo' produces two or more inflorescence with flowers having sepals and petals in the color of light yellow overlaid with pink toward the base, a purple red labellum, and a pink column. The inflorescence is strong, erect and sturdy, relatively short, and easily packaged for shipping. The plant grows very quickly to marketable size. 'Sogo Linluo' can be economically propagated via tissue culture.

What is claimed is:

1. A new and distinct cultivar of *Doritaenopsis* orchid plant named 'Sogo Linluo' as illustrated and described.

* * * * *